(12) United States Patent
Zalameda et al.

(10) Patent No.: US 7,855,368 B2
(45) Date of Patent: Dec. 21, 2010

(54) AIR-COUPLED ACOUSTIC THERMOGRAPHY FOR IN-SITU EVALUATION

(75) Inventors: Joseph N. Zalameda, Poquoson, VA (US); William P. Winfree, Williamsburg, VA (US); William T. Yost, Newport News, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 78 days.

(21) Appl. No.: 12/178,173

(22) Filed: Jul. 23, 2008

(65) Prior Publication Data

US 2010/0019153 A1 Jan. 28, 2010

(51) Int. Cl.
*G01J 5/02* (2006.01)
(52) U.S. Cl. ...................... 250/341.6; 374/46
(58) Field of Classification Search .............. 250/341.6; 374/46
See application file for complete search history.

(56) References Cited

U.S. PATENT DOCUMENTS

| | | | |
|---|---|---|---|
| 4,683,750 A | 8/1987 | Kino et al. | |
| 6,236,049 B1 | 5/2001 | Thomas et al. | |
| 6,399,948 B1 | 6/2002 | Thomas et al. | |
| 6,422,741 B2 | 7/2002 | Murphy et al. | |
| 6,543,287 B1 | 4/2003 | Davis | |
| 6,593,574 B2 | 7/2003 | Thomas et al. | |
| 6,730,912 B2 | 5/2004 | Sun et al. | |
| 6,751,342 B2 | 6/2004 | Shepard | |
| 6,786,098 B2 | 9/2004 | Bates | |
| 6,838,670 B2 | 1/2005 | Lewis et al. | |
| 6,877,894 B2 | 4/2005 | Vona et al. | |
| 6,951,134 B1 | 10/2005 | Mueller | |
| 7,057,176 B2 | 6/2006 | Rothenfusser et al. | |
| 7,060,971 B2 | 6/2006 | Zombo et al. | |
| 7,064,331 B2 | 6/2006 | Rothenfusser et al. | |
| 7,075,084 B2 | 7/2006 | Thompson et al. | |
| 7,083,327 B1 * | 8/2006 | Shepard ....................... | 374/46 |
| 7,119,338 B2 | 10/2006 | Thompson et al. | |
| 7,131,331 B2 | 11/2006 | Bates | |

(Continued)

OTHER PUBLICATIONS

Mayton et al. A design of experiments approach to characterizing the effects of sonic IR variables, Proc. of SPIE vol. 5405 (Apr. 2004), pp. 322-331.*

*Primary Examiner*—David P Porta
*Assistant Examiner*—Shun Lee
(74) *Attorney, Agent, or Firm*—Robin W. Edwards

(57) ABSTRACT

Acoustic thermography uses a housing configured for thermal, acoustic and infrared radiation shielding. For in-situ applications, the housing has an open side adapted to be sealingly coupled to a surface region of a structure such that an enclosed chamber filled with air is defined. One or more acoustic sources are positioned to direct acoustic waves through the air in the enclosed chamber and towards the surface region. To activate and control each acoustic source, a pulsed signal is applied thereto. An infrared imager focused on the surface region detects a thermal image of the surface region. A data capture device records the thermal image in synchronicity with each pulse of the pulsed signal such that a time series of thermal images is generated. For enhanced sensitivity and/or repeatability, sound and/or vibrations at the surface region can be used in feedback control of the pulsed signal applied to the acoustic sources.

34 Claims, 3 Drawing Sheets

U.S. PATENT DOCUMENTS

| | | |
|---|---|---|
| 7,297,952 B2 | 11/2007 | Raulerson et al. |
| 2001/0033669 A1* | 10/2001 | Bank et al. .................. 381/152 |
| 2004/0033313 A1* | 2/2004 | Niemiec ..................... 427/327 |
| 2004/0089812 A1* | 5/2004 | Favro et al. ............... 250/341.6 |
| 2005/0145794 A1* | 7/2005 | Faubion ...................... 250/330 |
| 2008/0022775 A1 | 1/2008 | Sathish et al. |

* cited by examiner

US 7,855,368 B2

AIR-COUPLED ACOUSTIC THERMOGRAPHY FOR IN-SITU EVALUATION

ORIGIN OF THE INVENTION

The present invention was made by employees of the United States Government and may be manufactured and used by or for the Government of the United States of America for governmental purposes without the payment of any royalties thereon or therefor.

BACKGROUND OF THE INVENTION

1. Field of the Invention

This invention relates to acoustic thermography. More specifically, the invention is a system and method for air-coupled acoustic thermography that can be used for in-situ evaluation of structures.

2. Description of the Related Art

Aircraft structures are increasingly being made from advanced composite sandwich structures typically defined by a lightweight core (e.g., a honeycomb) faced with thin composite skins. These structures are relatively inexpensive, lightweight, repairable, and can be molded into complex shapes. From time-to-time, aircraft incorporating these composite sandwich structures must be inspected for damage In particular, the skins or facing must be inspected, the bond between the skin/facings and the core must be inspected, and the core itself must be inspected. Since these structures are prone to moisture absorption through minute skin imperfections or damages, the inspection system must be sensitive. An effective inspection regimen and/or system must not only perform all of these inspections with a high-degree of sensitivity, but must do so in a non-destructive fashion while being performable "in the field" for a variety of types of composite sandwich structures.

A variety of known inspection regimens/testing systems have been used to inspect composite sandwich structures. Unfortunately, current approaches suffer from one or more drawbacks. For example, conventional ultrasonic inspection systems require direct contact with the structure and/or the use of a couplant (e.g., gel, water, etc.). Shearography illuminates a structure's surface with light and detects speckle interference patterns while a load (e.g., a vacuum) is applied to the structure's surface. However, it is difficult to determine defect size/shape through interpretation of fringe pattern data produced by this approach.

More recently, acoustic thermography has been used for flaw/damage detection. For example, U.S. Pat. No. 7,060,971 discloses a flaw inspection system that transmits ultrasonic waves towards a structure in order to generate a thermal signature that can be read by an infrared camera. Flaws or damages show up as "hot spots." However, reference blocks having known flaws/defects must be attached to the structure's surface in the area being inspected in order to assure that the proper amount of acoustic energy is being used. The continual need to attach/detach the reference blocks adds time and cost to the inspection regimen, poses risks of damage to the structure's surface, and presents problems for inspection repeatability.

Another acoustic inspection system method is disclosed in U.S. Pat. No. 7,297,952. A broadband acoustic signal is introduced into a structure where the signal includes at least two non-harmonically related frequencies. An infrared camera is used to capture both a background image and a series of images of the structure after the acoustic signal application. Correlations between the background image and series of images are performed on a pixel-by-pixel basis. However, this system is not sensitive enough for inspection of composite sandwich structures.

SUMMARY OF THE INVENTION

Accordingly, it is an object of the present invention to provide an acoustic thermography system and method for in-situ evaluation of a structure.

Another object of the present invention is to provide an acoustic thermography system and method having a high-degree of flaw/damage sensitivity.

Other objects and advantages of the present invention will become more obvious hereinafter in the specification and drawings.

In accordance with the present invention, an acoustic thermography system and method are provided. A housing is configured for thermal, acoustic and infrared radiation shielding. For in-situ applications, the housing has an open side adapted to be sealingly coupled to a surface region of a structure such that an enclosed chamber filled with air is defined by the housing and the surface region. At least one acoustic source supported by the housing is positioned to direct an acoustic wave therefrom through the air in the enclosed chamber and towards the surface region. To activate and control each acoustic source, a pulsed signal is applied thereto. The pulsed signal is defined by a time series of pulses having specified frequency, amplitude and phase. An infrared imager is focused on the surface region to detect a thermal image of the surface region. A data capture device records the thermal image in synchronicity with each pulse of the pulsed signal such that a time series of thermal images is generated. For enhanced sensitivity and/or repeatability, sound and/or vibrations at the surface region can be used in feedback control of the pulsed signal that is applied to the acoustic sources.

DETAILED DESCRIPTION OF THE INVENTION

Figure 1:
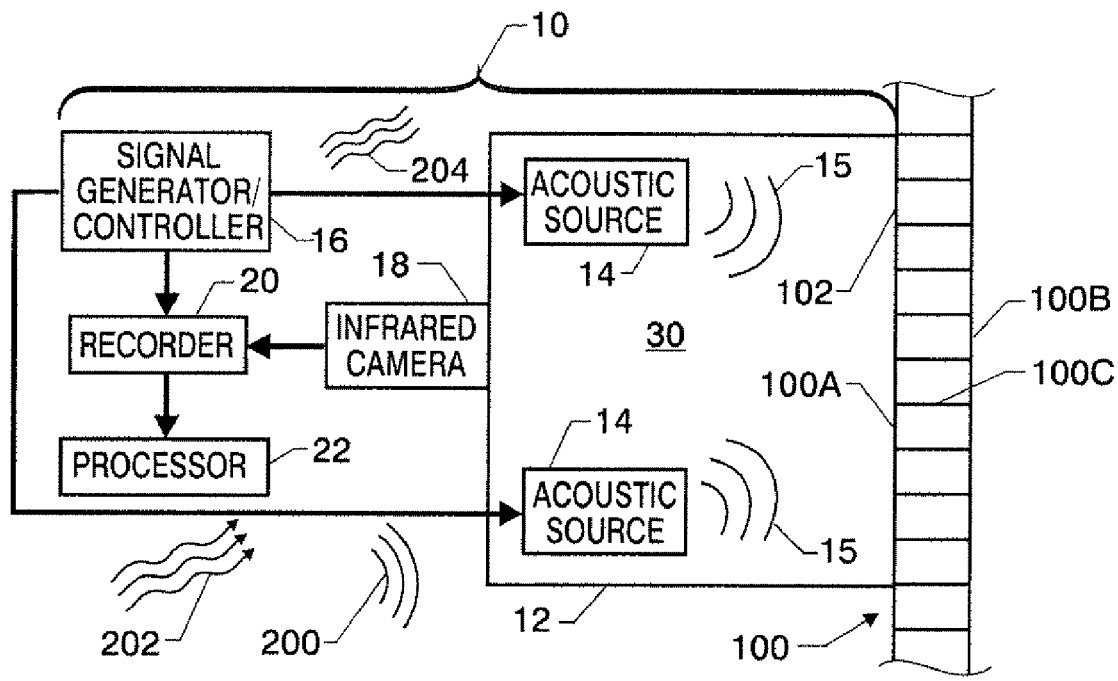
FIG. 1 is a schematic view of an acoustic thermography system in accordance with an embodiment of the present invention used for in-situ operation.

Referring now to the drawings and more particularly to FIG. 1, an in-situ air-coupled acoustic thermography system in accordance with an embodiment of the present invention is shown and is referenced generally by numeral 10. System 10 is positioned adjacent to a portion 102 of a structure 100. By way of example, portion 102 is a composite sandwich structure having facing skins 100A and 100B sandwiching a lightweight core 100C such as a honeycomb. However, it is to be understood that the particular construction of the structure is not a limitation of the present invention. In addition, facing skin 100A need not present a flat planar surface as system 10 can be readily configured to work on a contoured surface.

In the illustrated embodiment, acoustic thermography system 10 includes a housing 12, one or more acoustic sources 14, a signal generator/controller 16, an infrared camera 18, and a recorder 20. In general, system 10 produces and couples acoustic energy to portion 102 whereby the acoustic energy causes vibrations on and through portion 102. At a flaw or damage on/in portion 102, the vibrations cause heat to be generated that can be imaged by infrared camera 18. The present invention can cause and image such generated heat with improved sensitivity and repeatability when compared to prior art thermography systems. Improved sensitivity is important since even minor flaws/damages on composite sandwich structures can serve as a source of moisture intrusion. Improved repeatability of testing is important when similar structures must be evaluated for known/suspected flaws or damages as is often the case when a portion of a particular aircraft design must be evaluated.

Housing 12 is positioned adjacent to structure 100 and is in sealing contact with facing skin 100A such that an enclosed air-filled chamber 30 is defined by the combination of housing 12 and the enclosed region of facing skin 100A. Housing 12 is designed such that chamber 30 (and the region of facing skin 100A forming a portion of chamber 30) is isolated from external sources of acoustic noise (represented by wave lines 200), infrared radiation (represented by wavy arrows 202) and thermal energy (represented by wave lines 204). Housing 12 also contains acoustic waves 15 for reduced operator sound exposure.

Figure 2:
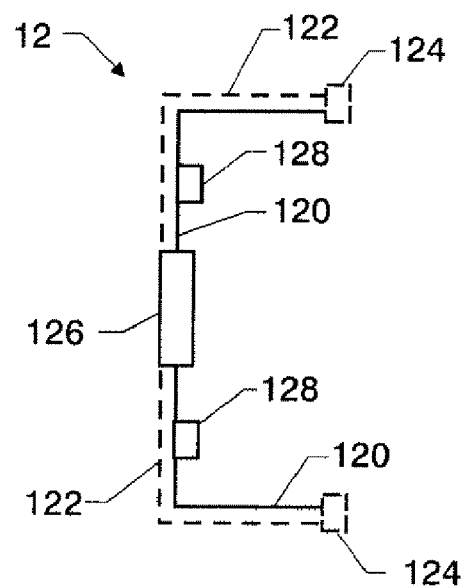
FIG. 2 is a cross-sectional schematic view of an isolation housing used to position acoustic sources near a structure in accordance with an in-situ embodiment of the present invention.

While housing 12 can be realized by a variety of constructions, one non-limiting example is illustrated schematically in FIG. 2 where housing 12 is constructed as an open-ended box. The internal regions 120 of housing 12 are made from an unpainted rigid metal having a low emissivity with respect to infrared radiation. For example, a shiny-surface aluminum is a good choice for internal regions 120 since aluminum is lightweight, readily available, and inexpensive. The external regions of housing 12 (represented by dashed lines 122) are made from insulation material(s) providing both acoustic and thermal insulation. For example, acoustic foam could provide both of these insulating properties. An annular seal 124 is provided around the open end of housing 12. Seal 124 could also be made from acoustic foam or another soft, sealing material thereby allowing housing 12 to readily adapt to contoured surfaces presented by facing skin 100A. An infrared window 126 can be provided in housing 12 so that infrared camera 18 can be located outside of housing 12. Mechanical supports or mounts 128 for acoustic sources 14 can be attached to internal regions 120.

Generally, acoustic sources 14 are supported by housing 12 in a position that allows acoustic waves 15 generated thereby to be transmitted through the air in chamber 30 and towards facing skin 100A. As will be explained further below, heating of portion 102 via acoustic waves 15 forms the basis of flaw or damage detection. In order to assure that such heating is only caused by acoustic waves 15 and not by any heat generated by acoustic sources 14, speakers having compression drivers are good choices for acoustic sources 14 since a compression driver speaker has its speaker coil oriented in a way that keeps it outside the thermal field of view. Each of acoustic sources can include an acoustic horn (not shown) to evenly disperse acoustic waves 15 within chamber 30.

Signal generator/controller 16 is any one or more devices that can generate and control a signal used to drive acoustic sources 14. The acoustic-source drive signals can be the same or different without departing from the scope of the present invention. In accordance with the present invention, the signals produced by generator/controller 16 are pulsed signals with the frequency, amplitude and phase thereof being specifically controlled. Precise control of the pulsed signals assures repeatability of testing procedures. This is important when multiple structures are to be evaluated in exactly the same fashion in order to inspect for a particular known type of flaw or damage that is evidenced by an acoustic signal having a particular frequency, amplitude and/or phase.

Infrared camera 18 is any conventional imaging system capable of detecting/imaging thermal energy on and in portion 102. Camera 18 can be mounted in housing 12 or outside thereof without departing from the scope of the present invention. To simplify adjustments of camera 18, housing 12 with infrared window 126 (FIG. 2) can be used so that camera 18 will be readily accessible after housing 12 is emplaced on structure 100.

Recorder 20 is any conventional device capable of storing data indicative a number of images provided thereto by camera 18. More specifically, recorder 20 records images from camera 18 in synchronicity with the pulses supplied to acoustic sources 14. Accordingly, signal generator/controller 16 also supplies its generated pulse train to recorder 20 as a trigger signal used to initiate the capture of images being imaged by camera 18. As a result, a time series of images are recorded in correspondence with the time series of pulses produced by generator/controller 16. Prior to activation of acoustic sources 14, a background image of portion 102 will typically be generated. That is, recorder 20 is used to record a reference image prior any acoustic heating of portion 102.

The images recorded by recorder 20 could be reviewed by one skilled in the analysis thereof. Additionally or alternatively, a processor 22 can be coupled to or incorporated with recorder 20 to automatically process the recorded image data. For example, the image data can be processed in the time domain using a fast Fourier transform algorithm to produce magnitude images as a function of frequency.

Figure 3:
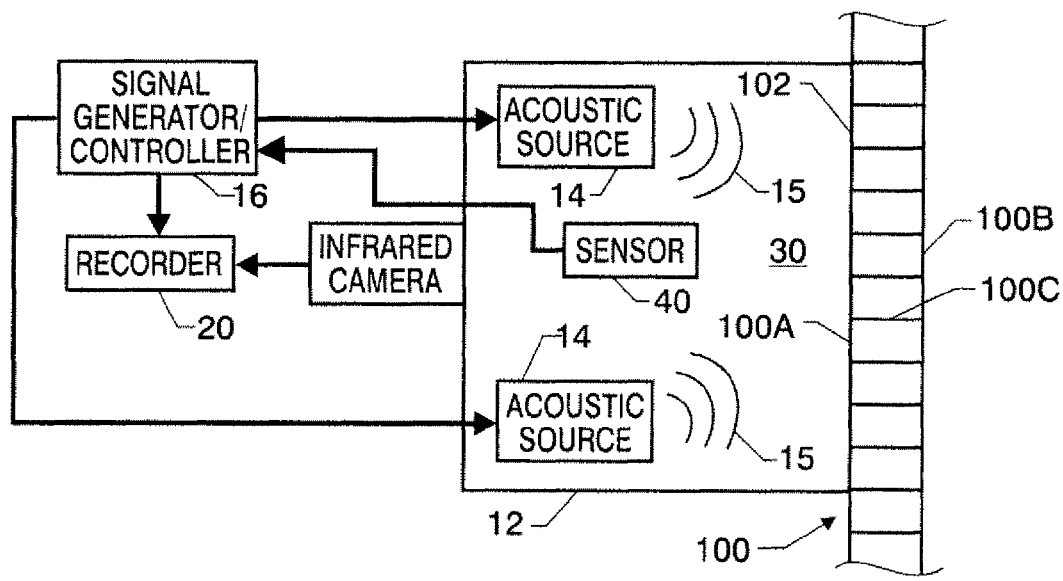
FIG. 3 is a schematic view of another embodiment of the acoustic thermography system to include feedback control.

The sensitivity and repeatability attributes of the present invention can be further enhanced via feedback control of signal generator/controller 16. Such feedback control is illustrated in FIG. 3 where a sound or vibration sensor 40 is positioned in chamber 30 a distance from facing skin 100A. Sensor 40 should be capable of detecting sound and/or vibration at the surface of facing skin 100A. For structures having known test histories, the sound/vibration levels at facing skin 100A are indicative of the level of sound energy being coupled to/through portion 102. Thus, the signal produced by sensor 40 can be used by generator/controller 16 to adjust the frequency, amplitude and/or phase of the signals applied to acoustic sources 14 until the desired sound/vibrations are detected by sensor 40. To detect sound in a non-contact fashion, sensor 40 could be a microphone. To detect vibrations in a non-contact fashion, sensor 40 could be a laser vibrometer. Both sound and vibrations sensors could also be used without departing from the scope of the present invention.

The advantages of the present invention are numerous. Evaluations performed by the present invention have detected surface damages, skin-to-core disbonds, and core damages. The system is sensitive to even small flaws/damages as outside sources of acoustic, thermal and infrared "noise" are excluded from the captured thermal images. Test repeatability is improved by the inclusion of feedback control of the pulsed signals used to drive the acoustic sources. The use of the insulating open-ended housing provides system portability so that a structure can be evaluated in-situ. The present invention is further discussed in J. N. Zalameda, W. P. Winfree, and W. T. Yost, "Air Coupled Acoustic Thermography (ACAT) Inspection Technique," AIP Conf. Proc. 975, 467 (2008), the contents of which are incorporated by reference in their entirety herein.

Figure 4:
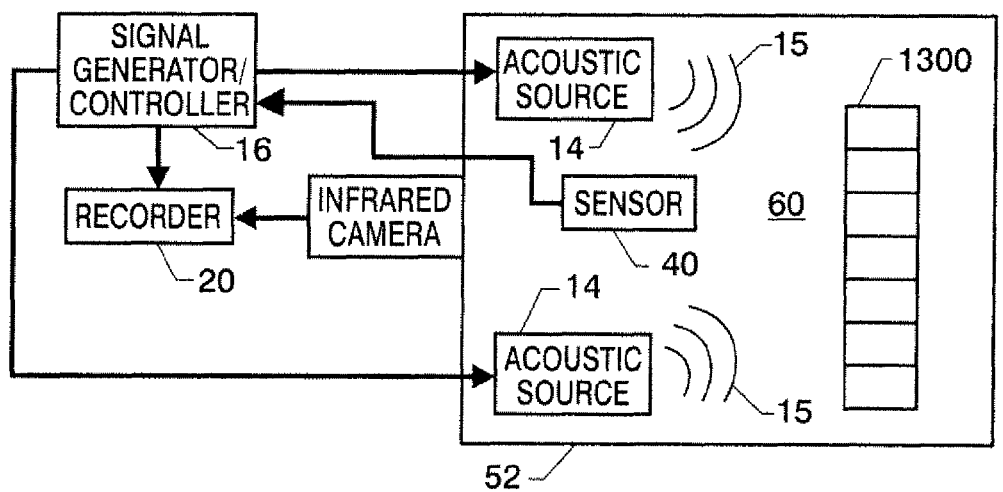
FIG. 4 is a schematic view of still another embodiment of the acoustic thermography system using a housing that completely encases a structure to be evaluated.
Figure 5:
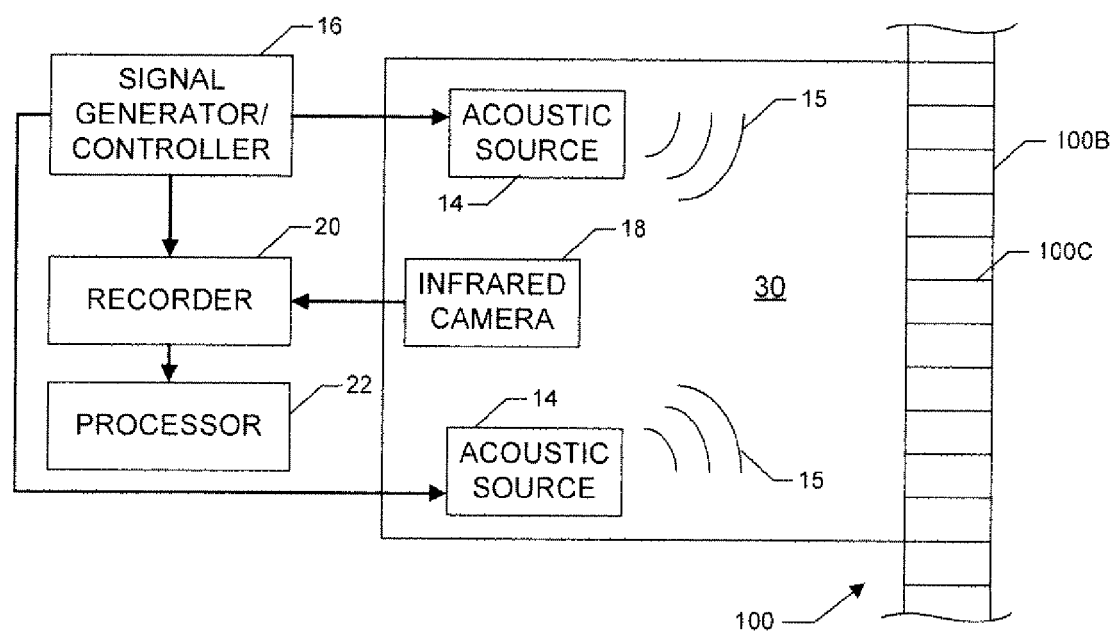
FIG. 5 is a schematic view of still another embodiment of the acoustic thermography system using an infrared camera within the housing.

Although the invention has been described relative to a specific embodiment thereof, there are numerous variations and modifications that will be readily apparent to those skilled in the art in light of the above teachings. For example, the present invention can be adapted for bench testing of smaller structures as shown in FIG. 4 where a housing 52 completely encases a structure 1300 to be evaluated within an air-filled chamber 60. Housing 52 can be constructed in a fashion similar to housing 12 in order to isolate chamber 60 from external sources of sound, heat and infrared radiation. It is therefore to be understood that, within the scope of the appended claims, the invention may be practiced other than as specifically described. As another example, the present invention can be adapted as shown in FIG. 5 where the infrared camera 18 is within the air-filled chamber 30 such that detecting the infrared image is carried out from within the air-filled chamber.

What is claimed as new and desired to be secured by Letters Patent of the United States is:

1. An acoustic thermography system, comprising:
    a housing configured for thermal, acoustic and infrared radiation shielding, said housing having an open side adapted to be sealingly coupled to a surface region of a structure wherein an enclosed chamber filled with air is defined by said housing and the surface region;
    at least one acoustic source supported by said housing and positioned to direct, when activated, an acoustic wave therefrom through the air in said enclosed chamber and towards the surface region;
    a signal controller, coupled to each said acoustic source, for generating a pulsed signal to activate and control each said acoustic source, said pulsed signal being defined by a time series of pulses having specified frequency, amplitude and phase;
    an infrared imager focused on the surface region and spaced apart therefrom detecting a thermal image of the surface region; and
    a data recorder coupled to said signal controller and said infrared imager for recording said thermal image in synchronicity with each of said pulses of said pulsed signal wherein a time series of thermal images is generated.

2. An acoustic thermography system as in claim 1, further comprising:
    a vibration sensor positioned in said enclosed chamber and spaced apart from the surface region for generating a signal indicative of vibrations at the surface region; and
    a controller coupled to said vibration sensor and said signal controller for controlling said frequency, said amplitude and said phase of said pulsed signal based on said signal from said vibration sensor.

3. An acoustic thermography system as in claim 1, further comprising:
    a microphone positioned in said enclosed chamber and spaced apart from the surface region for generating a signal indicative of sound at the surface region; and
    a controller coupled to said microphone and said signal controller for controlling said frequency, said amplitude and said phase of said pulsed signal based on said signal from said microphone.

4. An acoustic thermography system as in claim 1, further comprising a flexible seal formed about said open side of said housing wherein said flexible seal forms a sealing interface between said housing and the surface region.

5. An acoustic thermography system as in claim 1, further comprising an infrared window disposed in said housing wherein said infrared imager is positioned adjacent to said infrared window outside of said housing.

6. An acoustic thermography system as in claim 1, wherein each said acoustic source is an acoustic speaker having a compression driver.

7. An acoustic thermography system as in claim 1, wherein said data recorder records at least one background thermal image of the surface region prior to activation of each said acoustic source by said pulsed signal.

8. An acoustic thermography system as in claim 7, further comprising a processor for applying image processing techniques using said at least one background thermal image and said time series of thermal images.

9. An acoustic thermography system as in claim 1, wherein interior surfaces of said housing comprise metal and exterior surfaces of said housing comprise acoustic and thermal insulation.

10. An acoustic thermography system, comprising:
    a housing configured for thermal, acoustic and infrared radiation shielding, said housing having an open side adapted to be sealingly coupled to a surface region of a structure wherein an enclosed chamber filled with air is defined by said housing and the surface region;
    at least one acoustic source supported by said housing and positioned to direct, when activated, an acoustic wave therefrom through the air in said enclosed chamber and towards the surface region;
    a signal controller coupled to each said acoustic source for generating a pulsed signal to activate and control each said acoustic source, said pulsed signal being defined by a time series of pulses having specified frequency, amplitude and phase;
    an infrared imager focused on the surface region and spaced apart therefrom for detecting a thermal image of the surface region;
    a sensor positioned in said enclosed chamber and spaced apart from the surface region for generating a signal indicative of at least one of sound and vibrations at the surface region;
    said controller further coupled to said sensor for controlling said frequency, said amplitude and said phase of said pulsed signal based on said signal from said sensor; and
    a data recorder coupled to said signal controller and said infrared imager for recording (i) at least one background thermal image of the surface region prior to activation of each said acoustic source by said pulsed signal, and (ii) said thermal image in synchronicity with each of said pulses of said pulsed signal wherein a time series of thermal images is generated.

11. An acoustic thermography system as in claim 10, further comprising a flexible seal formed about said open side of said housing wherein said flexible seal forms a sealing interface between said housing and the surface region.

12. An acoustic thermography system as in claim 10, further comprising an infrared window disposed in said housing wherein said infrared imager is positioned adjacent to said infrared window outside of said housing.

13. An acoustic thermography system as in claim 10 wherein each said acoustic source is an acoustic speaker having a compression driver.

14. An acoustic thermography system as in claim 10, further comprising a processor for applying image processing techniques using said at least one background thermal image and said time series of thermal images.

15. An acoustic thermography system as in claim 10, wherein interior surfaces of said housing comprise metal and exterior surfaces of said housing comprise acoustic and thermal insulation.

16. A method for nondestructively recording data indicative of flaws on or within a structure, comprising the steps of:
enclosing at least a portion of a structure's surface region within an air-filled chamber that is substantially isolated from thermal, acoustic and infrared sources external to said chamber;
directing acoustic waves from within the air-filled chamber towards the surface region, said acoustic waves being controlled by at least one pulsed signal defined by a time series of pulses having specified frequency, amplitude and phase;
detecting an infrared image of the surface region;
detecting at least one of sound and vibrations at the surface region in a non-contact fashion;
controlling said frequency, said amplitude and said phase of said pulsed signal based on said at least one of sound and vibrations so-detected;
recording at least one background infrared image of the surface region prior to said step of directing; and
recording said infrared image in synchronicity with each of said pulses of said pulsed signal wherein a time series of thermal images is generated.

17. A method according to claim 16, wherein said step of enclosing comprises the step of encasing the entirety of the structure in the air-filled chamber.

18. A method according to claim 16, wherein said step of enclosing includes the step of incorporating said portion of the surface region as part of the air-filled chamber.

19. A method according to claim 16, wherein said step of detecting said infrared image is carried out from a location within the air-tilled chamber.

20. A method according to claim 16, wherein said step of detecting said infrared image is carried out from a location external to the air-filled chamber.

21. An acoustic thermography system for nondestructively recording data indicative of flaws on or within a structure, comprising:
a housing configured for thermal, acoustic and infrared radiation shielding, said housing enclosing the entirety of said structure within an enclosed chamber filled with air;
at least one acoustic source supported by and positioned within said housing and positioned to direct, when activated, an acoustic wave therefrom through the air in said enclosed chamber and towards the surface region;
a signal controller, coupled to each said acoustic source, for generating a pulsed signal to activate and control each said acoustic source, said pulsed signal being defined by a time series of pulses having specified frequency, amplitude and phase;
an infrared imager focused on the surface region and spaced apart therefrom for detecting a thermal image of the surface region; and
a data recorder coupled to said signal controller and said infrared imager for recording said thermal image in synchronicity with each of said pulses of said pulsed signal wherein a time series of thermal images is generated.

22. An acoustic thermography system as in claim 21, further comprising:
a vibration sensor positioned in said enclosed chamber and spaced apart from the surface region for generating a signal indicative of vibrations at the surface region; and
a controller coupled to said vibration sensor and said signal controller for controlling said frequency, said amplitude and said phase of said pulsed signal based on said signal from said vibration sensor.

23. An acoustic thermography system as in claim 21, further comprising:
a microphone positioned in said enclosed chamber and spaced apart from the surface region for generating a signal indicative of sound at the surface region; and
a controller coupled to said microphone and said signal controller for controlling said frequency, said amplitude and said phase of said pulsed signal based on said signal from said microphone.

24. An acoustic thermography system as in claim 21, further comprising an infrared window disposed in said housing wherein said infrared imager is positioned adjacent to said infrared window outside of said housing.

25. An acoustic thermography system as in claim 21, wherein each said acoustic source is an acoustic speaker having a compression driver.

26. An acoustic thermography system as in claim 21, wherein said data recorder records at least one background thermal image of the surface region prior to activation of each said acoustic source by said pulsed signal.

27. An acoustic thermography system as in claim 26, further comprising a processor for applying image processing techniques using said at least one background thermal image and said time series of thermal images.

28. An acoustic thermography system as in claim 21, wherein interior surfaces of said housing comprise metal and exterior surfaces of said housing comprise acoustic and thermal insulation.

29. An acoustic thermography system for nondestructively recording data indicative of flaws on or within a structure, comprising:
at least one acoustic source positioned to direct, when activated, an acoustic wave therefrom towards a surface region of the structure;
a signal controller, coupled to each said acoustic source, for generating a pulsed signal to activate and control each said acoustic source, said pulsed signal being defined by a time series of pulses having specified frequency, amplitude and phase;
an infrared imager focused on the surface region and spaced apart therefrom for detecting a thermal image of the surface region; and
a data recorder coupled to said signal controller and said infrared imager for recording said thermal image in synchronicity with each of said pulses of said pulsed signal wherein a time series of thermal images is generated.

30. An acoustic thermography system as in claim 29, further comprising:
a vibration sensor spaced apart from the surface region for generating a signal indicative of vibrations at the surface region; and
a controller coupled to said vibration sensor and said signal controller for controlling said frequency, said amplitude and said phase of said pulsed signal based on said signal from said vibration sensor.

31. An acoustic thermography system as in claim 29, further comprising:
a microphone spaced apart from the surface region for generating a signal indicative of sound at the surface region; and a controller coupled to said microphone and said signal controller for controlling said frequency, said amplitude and said phase of said pulsed signal based on said signal from said microphone.

32. An acoustic thermography system as in claim 29, wherein each said acoustic source is an acoustic speaker having a compression driver.

33. An acoustic thermography system as in claim 29, wherein said data recorder records at least one background thermal image of the surface region prior to activation of each said acoustic source by said pulsed signal.

34. An acoustic thermography system as in claim 33, further comprising a processor for applying image processing techniques using said at least one background thermal image and said time series of thermal images.

* * * * *